US010463757B2

(12) United States Patent
Lee et al.

(10) Patent No.: US 10,463,757 B2
(45) Date of Patent: Nov. 5, 2019

(54) AGENT FOR REMOVING MALODOR FROM PAINTING BOOTH, AND METHOD OF REMOVING MALODOR

(71) Applicants: HYUNDAI MOTOR COMPANY, Seoul (KR); Kyungpook National University Industry-Academic Cooperation Foundation, Daegu (KR)

(72) Inventors: Jae Seung Lee, Daegu (KR); Joong Kon Park, Daegu (KR); Min Ah Kim, Daegu (KR); Ye Ji Kim, Daegu (KR)

(73) Assignees: HYUNDAI MOTOR COMPANY, Seoul (KR); KYUNGPOOK NATIONAL UNIVERSITY ACADEMIC COOPERATION FOUNDATION, Daegu (KR)

( * ) Notice: Subject to any disclaimer, the term of this patent is extended or adjusted under 35 U.S.C. 154(b) by 38 days.

(21) Appl. No.: 15/729,184

(22) Filed: Oct. 10, 2017

(65) Prior Publication Data
US 2018/0028705 A1 Feb. 1, 2018

Related U.S. Application Data

(62) Division of application No. 14/871,772, filed on Sep. 30, 2015.

(30) Foreign Application Priority Data

Jan. 9, 2015 (KR) ........................ 10-2015-0003215

(51) Int. Cl.
| A61L 9/01 | (2006.01) |
| C12N 1/20 | (2006.01) |
| B01D 53/84 | (2006.01) |
| C02F 3/34 | (2006.01) |
| B01D 53/00 | (2006.01) |
| C02F 101/32 | (2006.01) |
| C02F 103/14 | (2006.01) |

(52) U.S. Cl.
CPC .............. *A61L 9/01* (2013.01); *B01D 53/00* (2013.01); *B01D 53/84* (2013.01); *C02F 3/341* (2013.01); *C12N 1/20* (2013.01); *B01D 2251/95* (2013.01); *B01D 2257/708* (2013.01); *B01D 2258/0258* (2013.01); *C02F 2101/322* (2013.01); *C02F 2103/14* (2013.01); *C02F 2303/02* (2013.01); *Y02A 50/235* (2018.01); *Y02A 50/2358* (2018.01)

(58) Field of Classification Search
CPC .. A61L 9/01; C12N 1/20; B01D 53/84; B01D 53/00; B01D 2251/95; B01D 2257/708; B01D 2258/0258; C02F 3/341; C02F 2101/322; C02F 2103/14; C02F 2303/02; Y02A 50/235; Y02A 50/2358
See application file for complete search history.

(56) References Cited

U.S. PATENT DOCUMENTS

| 8,071,342 B2 | 12/2011 | Herrema et al. |
| 2014/0091254 A1 | 4/2014 | Noland et al. |
| 2014/0120601 A1 | 5/2014 | Bywater-Ekegard et al. |

FOREIGN PATENT DOCUMENTS

| CN | 1445013 A | 10/2003 |
| CN | 1723762 A | 1/2006 |
| CN | 1973968 A | 6/2007 |
| CN | 101125280 A | 2/2008 |
| CN | 101538541 A | 9/2009 |
| CN | 101554485 A | 10/2009 |
| CN | 101812313 A | 8/2010 |
| CN | 101898084 A | 12/2010 |
| CN | 102114254 A | 7/2011 |
| CN | 102277312 A | 12/2011 |
| CN | 102344899 A | 2/2012 |
| CN | 102389701 A | 3/2012 |
| CN | 102430142 A | 5/2012 |
| CN | 103263846 A | 8/2013 |
| CN | 103627657 A | 3/2014 |
| CN | 1033649303 A | 3/2014 |
| CN | 104312938 A | 1/2015 |
| JP | H06-277045 A | 10/1994 |
| JP | 2003-010302 A | 1/2003 |
| JP | 2008-173562 A | 7/2008 |
| KR | 10-2003-0014186 A | 2/2003 |
| KR | 10-2004-0096824 A | 11/2004 |
| KR | 10-2005-0122668 A | 12/2005 |
| KR | 10-0748764 B1 | 8/2007 |
| KR | 10-2010-0005156 A | 1/2010 |
| KR | 10-2014-0108765 A | 9/2014 |

OTHER PUBLICATIONS

Bourque et al. Microbiological Degradation of Malodorous Substances of Swine Waste under Aerobic Conditions. Applied and Environmental Microbiology (1987), v53(1), p. 137-141. (Year: 1987).*
U.S. Non-Final Office Action dated May 2, 2017 issued in U.S. Appl. No. 14/871,772.
U.S. Final Office Action dated Oct. 25, 2017 issued in U.S. Appl. No. 14/871,772.
U.S. Office Action dated Aug. 24, 2018 issued in U.S. Appl. No. 14/871,772.
S. Boonchan, et al. "Surfactant-enhanced biodegradation of high molecular weight polycyclic aromatic hydrocarbons by stenotrophomonas maltophilia," (Abstract) Biotechnol Bioeng., Aug. 20, 1998, No. 59, vol. 4, pp. 482-494.

(Continued)

*Primary Examiner* — Sean C. Barron
(74) *Attorney, Agent, or Firm* — Morgan, Lewis & Bockius LLP

(57) ABSTRACT

An agent for removing malodor from a painting booth includes a volatile organic compound (VOC) degrading microorganism and a volatile fatty acid (VFA) degrading microorganism. The VOC degrading microorganism is configured to degrade VOC. The VFA degrading microorganism is configured to degrade VFA generated when the VOC is degraded. A method of removing malodor is also disclosed.

8 Claims, 6 Drawing Sheets

(56) References Cited

OTHER PUBLICATIONS

C. C. Chang, et al., "Hydrogenotrophic denitrification with immobilized Alcaligenes eutrophus for drinking water treatment," Bioresource Technology, 1999, vol. 69, pp. 53-58.
D. Bourque, et al., "Microbiological Degradation of Malodorous Substances of Swine Waste under Aerobic Conditions," Applied and Environmental Microbiology, 1987, vol. 53, pp. 137-141.

\* cited by examiner

AGENT FOR REMOVING MALODOR FROM PAINTING BOOTH, AND METHOD OF REMOVING MALODOR

CROSS-REFERENCE TO RELATED APPLICATION

This application is a divisional patent application of U.S. patent application Ser. No. 14/871,772, filed on Sep. 30, 2015, which claims under 35 U.S.C. § 119(a) the benefit of priority to Korean Patent Application No. 10-2015-0003215 filed on Jan. 9, 2015, their entire contents of which are incorporated herein by reference.

TECHNICAL FIELD

The present disclosure relates to an agent and method for removing malodor from a painting booth. The agent includes a volatile organic compound (VOC) degrading microorganism and a volatile fatty acid (VFA) degrading microorganism.

BACKGROUND

In a painting process of vehicles and the like, a large amount of water is provided in the form of a water curtain into a painting booth to remove excess spray-paint generated in the painting booth. The water provided in the form of a water curtain is contacted with the excess spray-paint, mixed, and then recovered in a water tank of a circulating water system through a water channel. In the circulating water recovered in the water tank, the excess spray-paint and organic solvents are contained. Thus, a process of separating and recovering the paint and organic solvents contained in the circulating water by a purification process, and then providing the purified circulating water again to the painting booth is repeated.

At this time, malodor is generated by the organic solvents and the like contained in the circulating water. However, the conventional chemicals or agents containing microorganism, disclosed in Korean Patent Publication No. 10-0748764 and the like, have meager malodor removing effect, and therefore, it does not satisfy a legal allowance of the reinforced environmental regulation, thereby causing problems on factory operation. Thus, it is urgent to suggest alternatives.

The above information disclosed in this Background section is only for enhancement of understanding of the background and therefore it may contain information that does not form the prior art that is already known in this country to a person of ordinary skill in the art.

SUMMARY

The present disclosure has been made in an effort to solve the above-described problems associated with prior art.

An object of the present disclosure is to provide a complex agent containing microorganism, which can effectively degrade VOC and VFA as a malodor generating material, and a method of removing malodor using thereof.

The object of the present disclosure is not limited to the above-described object, and other objects of the present disclosure that have not been described will be clearly understood by the following description.

To achieve the above objects, various embodiments of the present invention include the following constituents.

In one aspect, the present disclosure provides an agent for removing malodor from a painting booth. The agent includes a volatile organic compound (VOC) degrading microorganism configured to degrade VOC and a volatile fatty acid (VFA) degrading microorganism configured to degrade VFA generated when the VOC is degraded.

In certain embodiments, the VOC degrading microorganism may comprise at least one of *Pseudomonas putida, Pseudomonas stutzeri* and *Bacillus cereus*.

In certain embodiments, the VOC degrading microorganism may further include *Mycobacterium* sp., *Pseudomonas* sp., *Stenotrophomonas maltophilia*, is *Burkholderia cepacia* and *Pseudomonas fluorescens*

In certain embodiments, the VFA degrading microorganism may include at least one of *Bacillus tequilensis, Alcaligenes eutrophus* and *Alcaligenes faecalis*.

In certain embodiments, the VFA degrading microorganism may further include at least one of *Pseudomonas* sp., *Bacillus cereus* and *Bacillus megaterium*.

In certain embodiments, the VOC may be toluene or xylene.

In certain embodiments, the VFA may be acetic acid, pentanoic acid, butyric acid or propionic acid.

In certain embodiments, a mixing ratio of the VOC degrading microorganism may be adjusted according to ingredients of the VOC.

In certain embodiments, a mixing ratio of the VFA degrading microorganism may be adjusted according to ingredients of the VFA.

In another aspect, the present disclosure provides a method of removing malodor. The method includes applying a malodor removing agent to a malodor generating material, where the malodor removing agent includes a VOC degrading microorganism and a VFA degrading microorganism. The VOC degrading microorganism is configured to degrade VOC. The VFA degrading microorganism, is configured to degrade VFA generated when the VOC is degraded.

Other aspects and embodiments of the invention are discussed infra.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

BRIEF DESCRIPTION OF THE DRAWINGS

Certain features of the present invention will now be described in detail with reference to certain exemplary embodiments thereof illustrated the accompanying drawings which are given hereinbelow by way of illustration only, and thus are not limitative of the present invention, and wherein.

Figure 1:
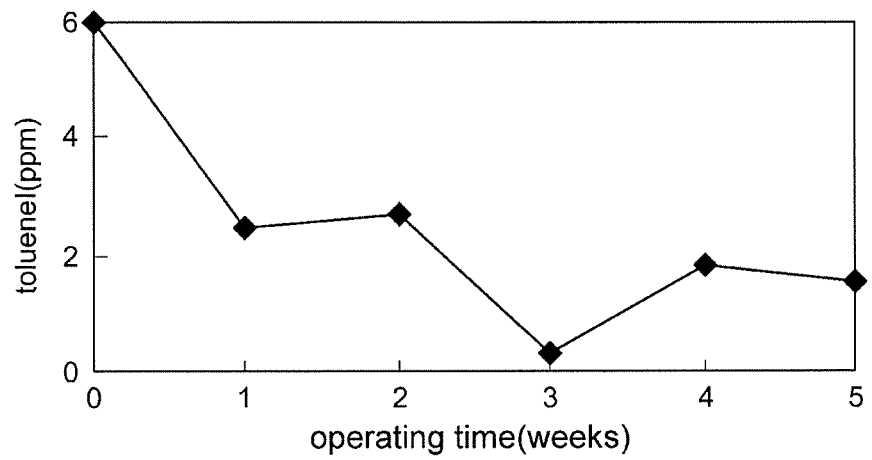
FIG. 1 is a graph illustrating toluene concentration according to Example 1.

It should be understood that the appended drawings are not necessarily to scale, presenting a somewhat simplified representation of various preferred features illustrative of the basic principles of different embodiments of the invention. The specific design features of embodiments of the present invention as disclosed herein, including, for example, specific dimensions, orientations, locations, and shapes will be determined in part by the particular intended application and use environment.

In the figures, reference numbers refer to the same or equivalent parts throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The painting used in a vehicle painting factory contains a large amount of organic solvent, and the organic solvent often includes volatile organic compounds (VOC) such as toluene, xylene, benzene, ethyl benzene and the like.

The VOC is harmful to the human body and also causes strong malodor even in a low concentration. Thus, an effective removing is needed. Accordingly, a painting factory has operated a biological treatment facility as a pollutant discharge prevention facility, but it did not satisfy a reinforced environmental regulation for pollutants due to its low degradation efficiency, and also did not consider VFA generated during the VOC degradation process at all.

The VFA is a material such as acetic acid, pentanoic acid, butyric acid or propionic acid and the like, and it generates strong malodor even in a trace amount because it has very low odor threshold concentration, i.e., about 1/100 to 1/1000 of that of the VOC. Thus, for effectively removing malodor from the painting booth, degradation of the VFA as well as removal of the VOC is definitely needed.

EXAMPLES

The following examples illustrate embodiments of the invention and are not intended to limit the invention.

Example 1

Biological Treatment of VOC

Biological treatment of booth circulating water was conducted by using circulating water really used in a painting booth and air of an exhaust pipe as a sample.

For biological treatment of the circulating water, a Cumtom FM agent containing microorganism from Custom Bio™ was injected, and the agent containing microorganism of total 3000 kg was continuously injected for 5 weeks at flow rate of 60 to 120 kg/day.

Toluene concentration and xylene concentration in the circulating water, total hydrocarbon (THC) of the exhaust pipe, and malodor concentration of the exhausted air from the exhaust pipe were measured every week from the first day of the agent containing microorganism injection.

Figure 2:
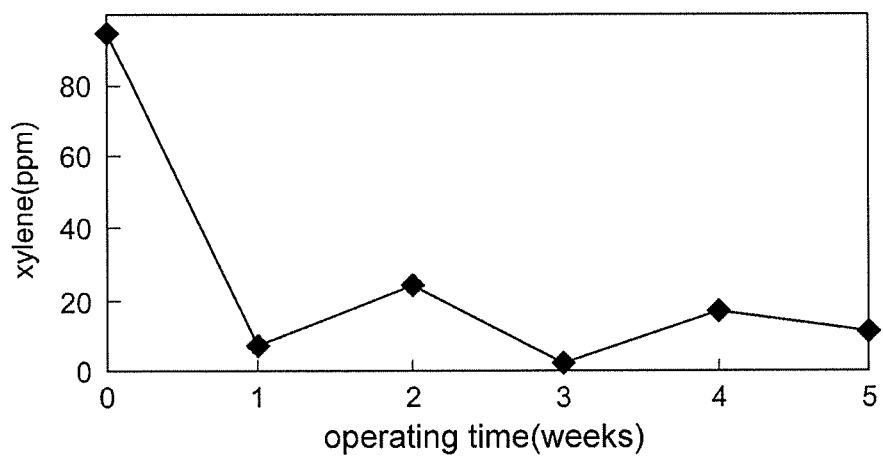
FIG. 2 is a graph illustrating xylene concentration according to Example 1.
Figure 3:
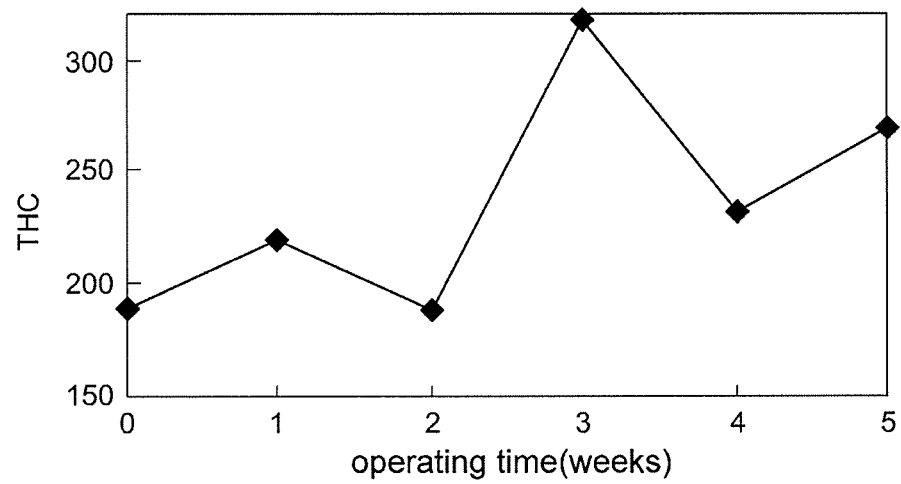
FIG. 3 is a graph illustrating total hydrocarbon (THC) concentration according to Example 1.
Figure 4:
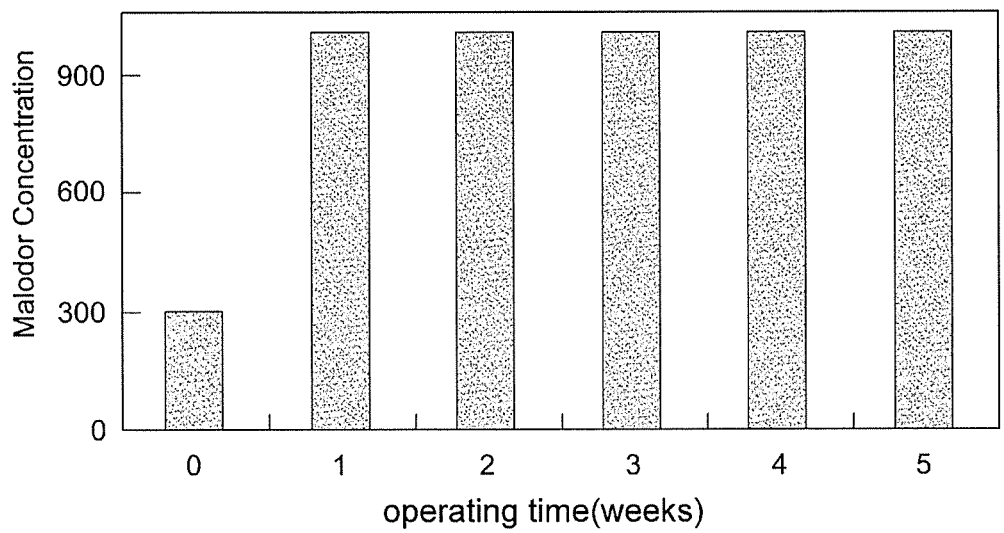
FIG. 4 is a graph illustrating malodor concentration according to Example 1.

Referring to FIG. 1 and FIG. 2, the concentrations of toluene and xylene that are VOC in the circulating water were tend to be reduced as time goes on, but referring to FIG. 3, the THC in the air was tend to be increased as time goes on, and the malodor concentration was also increased at the same time as shown in FIG. 4.

Through this, it could be found that the malodor in the painting booth cannot be removed by only removing the VOC.

Example 2

VOC Degradation Using VOC Degrading Microorganism

Toluene and xylene degradation effect of the VOC degrading microorganism according to embodiments of the present invention and generation of VFA according to the VOC degradation were tested.

The VOC degrading microorganisms used in Example 2 were as shown in the following Table 1.

TABLE 1

| VOC degrading microorganism | |
|---|---|
| *Pseudomonas putida* | Toluene, Ethylbenzene Degradation |
| *Pseudomonas stutzeri* | Toluene, Xylene, Benzene, Ethylbenzene Degradation |
| *Bacillus cereus* | Xylene Degradation |

50 ml nutrient agar medium was put into a 250 ml Erlenmeyer flask, each 50 ppm of toluene and xylene were injected thereto, respectively, the VOC degrading microorganism of 5 v/v % was added thereto, and then stirred for 2 days at 25° C., 100 rpm. The concentrations of toluene and xylene were measured by collecting liquid and gas samples.

Figure 5:
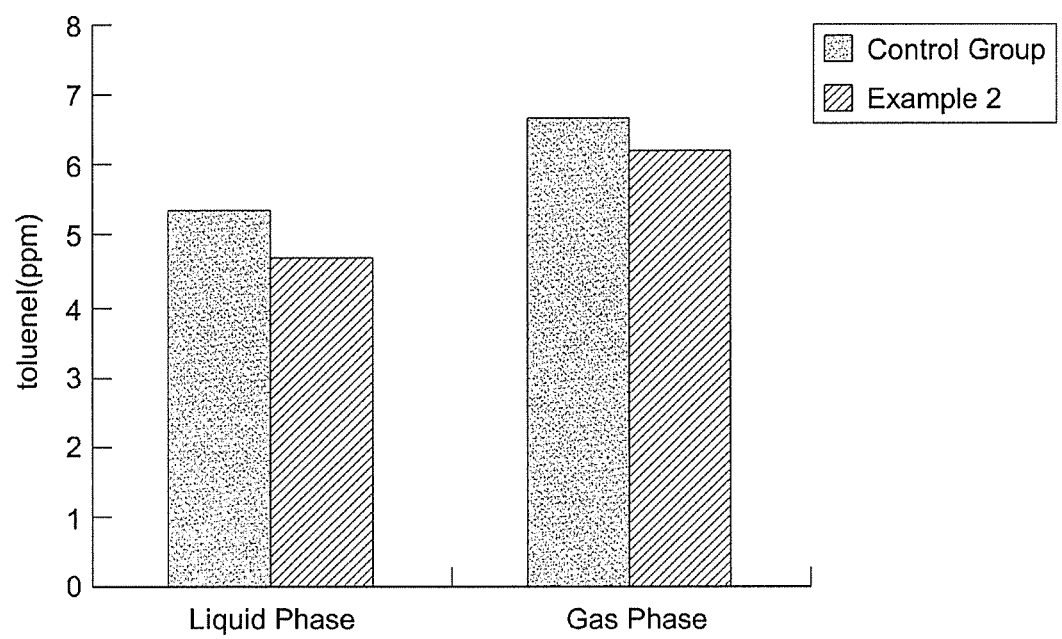
FIG. 5 is a graph illustrating toluene concentration according to Example 2.

Referring to FIG. 5, it could be found that the toluene concentration was reduced 0.645 ppm, 12% at liquid phase and 0.500 ppm, 7.5% in gas phase, compared to the control group that is not added with the VOC degrading microorganism in Example 2.

Figure 6:
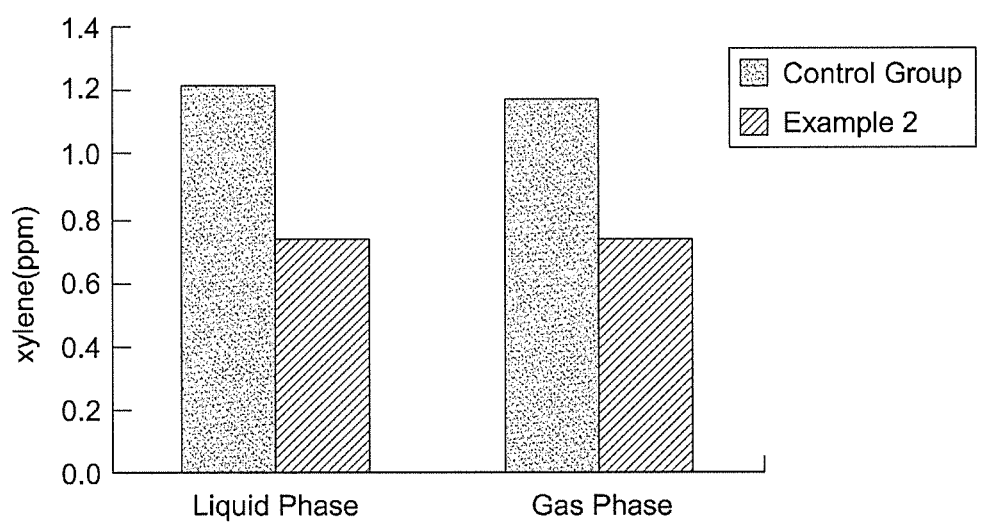
FIG. 6 is a graph illustrating xylene concentration according to Example 2.

Referring to FIG. 6, it could be found that the xylene concentration was reduced 0.476 ppm, 39.8% in liquid phase and 0.403 ppm, 37% in gas phase, compared to the control group in Example 2.

Figure 7:
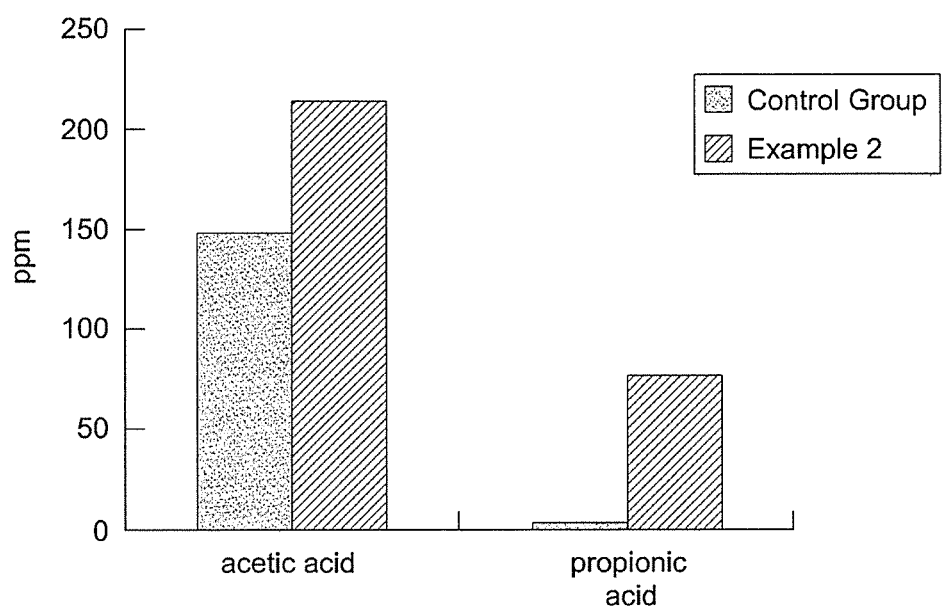
FIG. 7 is a graph illustrating acetic acid and propionic acid concentrations according to Example 2.

Further, referring to FIG. 7, it could be found that the acetic acid concentration was increased 66.5 ppm, 145%, and the propionic acid concentration was increased 72.9 ppm, 3000%, compared with the control group in Example 2.

Namely, it could be found that when degrading the VOC by adding only the VOC degrading microorganism, the VFA as a malodor generating material such as acetic acid and propionic acid is generated. Thus, it could be found that the VFA should be degraded in order to remove malodor from the painting booth, from increase of the THC concentration and the malodor concentration in Example 1.

Example 3

VOC Degradation Using VOC Degrading Microorganism and VFA Degradation Using VFA Degrading Microorganism VOC (toluene, xylene) degradation effect of the VOC degrading microorganism according to embodiments of the present invention and degradation effect of VFA (acetic acid, propionic acid), generated during the VOC degradation process, of the VFA degrading microorganism were tested.

In Example 3, as the VOC degrading microorganism, the microorganism group of Table 1 above, and as the VFA degrading microorganism, the microorganism group of Table 2 below were used.

TABLE 2

| VFA degrading microorganism | |
| --- | --- |
| Bacillus tequilensis | Acetic acid, Butyric acid Degradation |
| Alcaligenes eutrophus | Acetic acid, Propionic acid, Butyric acid Degradation |
| Alcaligenes faecalis | Acetic acid, Propionic acid Degradation |

50 ml nutrient agar medium was put into a 250 ml Erlenmeyer flask, each 50 ppm of toluene and xylene were injected thereto, respectively, the VOC degrading microorganism of 5 v/v % and the VFA degrading microorganism of 5 v/v % were added thereto, and then stirred for 2 days at 25° C., 100 rpm. The concentrations of VOC and VFA were measured by collecting a liquid sample.

Figure 8:
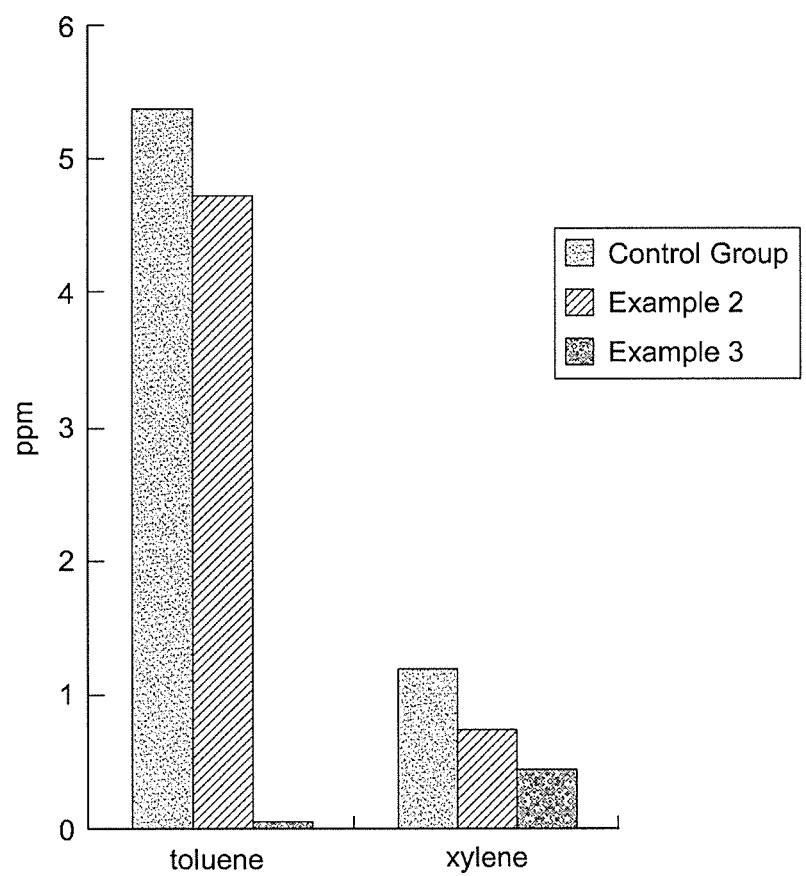
FIG. 8 is a graph illustrating toluene and xylene concentrations according to Example 3.
Figure 9:
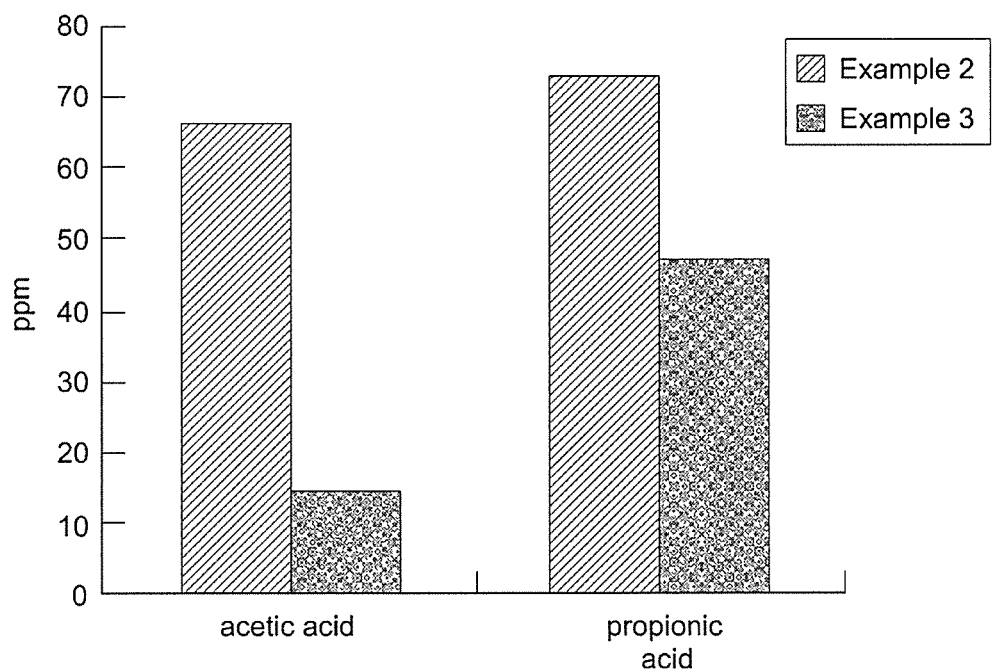
FIG. 9 is a graph illustrating acetic acid and propionic acid concentrations according to Example 3.

Referring to FIG. 8, it could be found that when comparing Example 3 with the control group, the toluene concentration in Example 3 was reduced 5.312 ppm, 99.1%, and the xylene concentration was reduced 0.76 ppm, 63.6%. Further, referring to FIG. 9, it could be found that when comparing Example 3 with Example 2, the acetic acid concentration was reduced 52.2 ppm, 78.6%, and the propionic acid concentration was reduced 25.8 ppm, 35.4%.

Through this, it could be found that the VOC can be degraded, and the VFA, which is generated during the VOC degradation process, also can be degraded by adding the VFA degrading microorganism together with the VOC degrading microorganism, thereby effectively removing malodor in the painting booth.

The agent of the present invention is not limited to the embodiments used in the above examples. In certain embodiments, the VOC degrading microorganism may further include *Mycobacterium* sp., *Pseudomonas* sp., *Stenotrophomonas maltophilia*, *Burkholderia cepacia* or *Pseudomonas fluorescens* having an ability of degrading the VOC. In certain embodiments, the VFA degrading microorganism may further include *Pseudomonas* sp., *Bacillus cereus* or *Bacillus megaterium* having an ability of degrading the VFA.

Thus, according to certain embodiments of the present invention, the VOC that is a malodor generating material contained in circulating water of a painting booth and the like is removed by the VOC degrading microorganism, and the VFA that is a strong malodor material generated during the VOC degradation process can be removed by the VFA degrading microorganism, and therefore, the malodor problem from the painting booth can be solved.

Further, in the VOC degrading microorganism and the VFA degrading microorganism, which are included in the agent containing microorganism according to embodiments of the present invention, which microorganism can be degraded by each microorganism can be checked. Thus, malodor can be removed more effectively by measuring the VOC concentration and the VFA concentration contained in each painting booth and then adjusting the mixing ratio of the agent containing microorganism according to its ingredients.

For example, in the case of the painting booth using a paint with high toluene content, in certain embodiments, the malodor removing effect can be increased by mixing design such as increasing composition of *Pseudomonas putida* and the like, which degrades toluene.

When using the agent containing microorganism for removing malodor according to certain embodiments of the present invention, which has the constitution described above, malodor from a painting booth can be effectively removed by degrading VOC and VFA, malodor generating materials.

The agent containing microorganism for removing malodor according to certain embodiments of the present invention has an effect of completely removing malodor from a painting booth because it can remove VFA causing severe malodor, which is 100 to 500 times stronger than VOCs, unlike the conventional biological treating agent.

The invention has been described with reference to exemplary embodiments thereof. However, it will be appreciated by those skilled in the art that changes may be made in these embodiments without departing from the principles and spirit of the invention, the scope of which is defined in the appended claims and their equivalents.

What is claimed is:

1. A method of removing malodor from a painting booth, the method comprising:
    applying a malodor removing agent to a malodor generating material,
    wherein the malodor removing agent comprises a volatile organic compound (VOC) degrading microorganism and a volatile fatty acid (VFA) degrading microorganism,
    the VOC degrading microorganism is configured to degrade VOC, and comprises *Pseudomonas* putida and *Stenotrophomonas maltophilia*, and
    the VFA degrading microorganism is configured to degrade VFA which is generated when the VOC is degraded, and comprises *Alcaligenes eutrophus* and *Bacillus* megaterium.

2. The method of claim 1, wherein the VOC degrading microorganism further comprises at least one of *Pseudomonas* stutzeri or *Bacillus cereus*.

3. The method of claim 2, wherein the VOC degrading microorganism further comprises at least one of *Mycobacterium* sp., *Pseudomonas* sp., *Burkholderia cepacia* or *Pseudomonas fluorescens*.

4. The method of claim 1, wherein the VFA degrading microorganism further comprises *Bacillus* tequilensis or *Alcaligenes* faecalis.

5. The method of claim 4, wherein the VFA degrading microorganism further comprises *Pseudomonas* sp. or *Bacillus cereus*.

6. The method of claim 1, wherein the VOC includes toluene or xylene.

7. The method of claim 1, wherein the VFA includes acetic acid, pentanoic acid, butyric acid or propionic acid.

8. The method of claim 1, wherein the VOC includes benzene or ethyl benzene.

* * * * *